US006387847B1

(12) United States Patent
Yvin et al.

(10) Patent No.: US 6,387,847 B1
(45) Date of Patent: May 14, 2002

(54) METHOD FOR STIMULATING NATURAL CONTROL SYSTEM OF PLANTS

(75) Inventors: Jean-Claude Yvin; Florence Cruz; Jean-Marie Joubert, all of Saint-Malo; Bernard Cloarec, Saint Pol De Leon; Christophe Richard, Plougourvest; Bertrand Plesse, Strasbourg; Marguerite Kopp, Wolxheim; Bernard Fritig, Souffelweyersheim, all of (FR)

(73) Assignee: Laboratoires Goemar S.A., Saint Malo (FR)

( * ) Notice: Subject to any disclaimer, the term of this patent is extended or adjusted under 35 U.S.C. 154(b) by 0 days.

(21) Appl. No.: 09/463,065

(22) PCT Filed: Jul. 20, 1998

(86) PCT No.: PCT/FR98/01590

§ 371 Date: Mar. 31, 2000

§ 102(e) Date: Mar. 31, 2000

(87) PCT Pub. No.: WO99/03346

PCT Pub. Date: Jan. 28, 1999

(30) Foreign Application Priority Data

Jul. 18, 1997 (FR) .............................. 97 09168

(51) Int. Cl.$^7$ .................. A01N 43/16; A01N 63/02; A01N 63/04
(52) U.S. Cl. .................. 504/117; 504/292; 504/294
(58) Field of Search .................. 504/117, 292, 504/294

(56) References Cited

U.S. PATENT DOCUMENTS 5,750,472 A   5/1998   Yvin et al. .................. 504/292

FOREIGN PATENT DOCUMENTS

| FR | 2 693 454 | 1/1994 |
| JP | 06239880 | 5/1991 |
| WO | WO 93/06730 | 4/1993 |

OTHER PUBLICATIONS

Rouhier et al. Structural features of fungal B–D–glucans for the efficient inhibition of the initiation of virus infection on *Nicotiana tabacum*. Phytochemistry. 39(1):57–62, 1995.*
Mohr et al. Plant Physiology. Springer. p. 558–566, 1995.*
Albersheim, P. et al.: "Plants Interact with Microbial Polysaccharides" XP002061730; (1977) J. Supramol. Struct, vol. 6, No. 4, pp. 599–616; Biological Abstracts, vol. 65, Philadelphia, PA, U.S.; Abstract No. 54923.

Ozeretskovskaya, O.L. et al.: "Oligosaccharins as Regulatory Molecules of Plants" (1996) Russian Journal of Plant Physiology, vol. 43, No. 5, pp. 648–655, XP002061729.
Meiji Seika Kaisha: "Oligosaccharide Preparation Hydrolysis Beta Glucan Contain Water Soluble Polysaccharide Solvent Precipitation" (Sep. 27, 1990) Database WPI Section Ch. Week 9045 Derwent Publications Ltd., London, GB; Class B03, AN 90–338512 XP 002061732 & JP 02 243697 A. (Abstract).
Taito KK: "Preparation Low Molecular Branch Chain Beta Glucan Branch Chain Oligosaccharide React Endo Type Beta Glucanase Triple Helical Structure Branch Chain Beta Glucan" (Oct. 4, 1994) Database WPI Section Ch. Week 9444 Derwent Publications Ltd., London, GB; Class B04, AN 94–353761 XP 002061733 & JP 06 277085 A.
Huncikova, S. et al. (Ustav Experimentalnej Fytopatologie): "Plant Virus Infect Prevent Composition Comprise Dilute Aqueous Solution Water Soluble Yeast Derivative Glucan Mannan" (Nov. 18, 1992) Database WPI Section Ch. Week 9313 Derwent Publications Ltd., London, GB; Class C03, AN 93–101689 XP 002061734 & CS 9 101 053 A.
Heinkel, C.M. et al.: "Further Characterization of Mycolaminaran–Induced Resistance: Temperature Sensitivity Against Tobacco Mosaic Virus and Function Against Cauliflower Mosaic Virus and Tomato Spotted Wilt Virus" (Oct. 12, 1992) Chemical Abstracts, vol. 117, No. 15, Columbus, Ohio, U.S.; Abstract No. 147017XP002061731 Phytopathology, vol. 82, No. 6, pp. 637–641. (Abstract).
Rouhier, P. et al.: "Structural Features of Fungal Beta–D–Glucans for the Efficient Inhibition of the Initiation of Virus Infection on Nicotiana Tabacum" (1995) Database Cropu STN–International STN–Accession No. 95–84943, XP002085178 Phytochemistry vol. 39, No. 1, pp. 57–62. (Abstract).
Seifert, K. et al.: "Phytoalexin Accumulation in Ornithopus sativus as a Response to Elicitor Treatment" (1993) Database Cropu STN–International STN–Accession No. 93–86799, XP002085179 Z. Naturforsch. C, vol. 48, No. 7–8, pp. 550–555 (Abstract).

* cited by examiner

*Primary Examiner*—S. Mark Clardy
(74) *Attorney, Agent, or Firm*—Kilpatrick Stockton LLP

(57) ABSTRACT

The present invention provides a method to potentiate and stimulate natural defensive reactions of plants to a pathogenic agent. The method comprises application to plants of a composition comprising an effective amount of one or more oligo β 1–3 glucans composed of 3 to 250 monosaccharide units and a vehicle, wherein the effective amount of oligo β 1–3 glucans in the composition does not directly stimulate natural defensive reactions of plants when the pathogenic agent is absent.

17 Claims, No Drawings

METHOD FOR STIMULATING NATURAL CONTROL SYSTEM OF PLANTS

A subject matter of the invention is a process for potentiating and stimulating the natural defenses of plants of the type of those which are agronomically useful.

It relates in particular to the vine and fruit trees of the group comprising the apple tree and the pear tree, to cereals of the group comprising wheat, maize and rice, to oleaginous plants of the group comprising soya, sunflower and rape, and to vegetable plants of the group comprising carrots, cauliflower, tomatoes and potatoes.

The stimulation of the natural defenses of plants is one of the most topical problems and forms the subject of a great deal of research.

The stimulation of the natural defenses is reflected, in the case of a plant which has had an initial contact with a pathogenic agent, such as a virus, a bacterium, a fungus or an insect, by the development of a set of biological modifications which confer, on this plant, a presensitization by virtue of which it becomes capable of reacting more effectively to a fresh attack.

The research studies discussed above have made it possible to demonstrate that the presensitization can be obtained by bringing the plant into contact with certain synthetic chemicals.

Furthermore, products called elicitors are known which, when brought into contact with the plant, are capable of stimulating, in the latter, defensive reactions of the type:

accumulation of natural antibiotics better known under the name of phytoalexins, synthesis of defensive proteins, such as chitinases or glucanases, also known under the name of PRP (Pathogenesis-related proteins), hardening of the cell walls by synthesis of lignin or of crosslinking proteins, synthesis of secondary messengers, such as ethylene, hydrogen peroxide or salicylic acid.

Mention may in particular be made among these products, of oligo β 1–3 glucans, which elicit the defensive reactions in question in various agronomically useful plants; the maximum responses are generally achieved when the oligo β 1–3 glucans are employed either in the form of liquid compositions, which comprise them at concentrations of the order of 200 mg/l, and they are maintained at a comparable level up to concentrations of the order of 4 g/l, or in amounts per hectare of 4 to 200 g.

There are a number of disadvantages to proceeding in this way, which results in the deployment of defensive reactions in the absence of any pathogenic agent, among which disadvantages may be mentioned a not insignificant energy expense for the plant.

The aim of the invention is therefore, in particular, to make available to users novel means which make it possible to arrange for the stimulation of the natural defenses of the plant only to take place in the event of need, in other words during attack on the plant by a pathogenic agent, these means consequently conferring the abovementioned acquired systemic resistance, in other words an immunity against pathogenic agents, on the plant.

And it is to the credit of the Applicant Company to have found, as a result of intensive research, that, entirely surprisingly and unexpectedly, not only is this result achieved but that a potentiation of the natural defenses even takes place as soon as a composition is applied to a plant of the type in question comprising one or more oligo β 1–3 glucans composed of 3 to 250, preferably of 3 to 50 and more preferably of 3 to 30 monosaccharide units, their molecular masses consequently ranging from 540 to 45,000 Daltons, these oligo β 1–3 glucans being present in the composition at concentrations lower than those which directly induce defensive reactions, these concentrations being of the order of 1 to 20 mg/l, preferably of 2 to 10 mg/l in the case of wheat and tobacco, which corresponds to the use per hectare of crop of an amount of 1 to 200 g, preferably of 4 to 80 g, of the abovedefined oligo β 1–3 glucans.

This is because it has been able to show that, when the aforesaid oligo β 1–3 glucans are used in the form of compositions in which they are present at concentrations lying within a narrow range from 1 to 20 mg/l in the case of wheat and tobacco, which corresponds to the use per hectare of crop of the amounts indicated above, they exert, on the treated plants, a potentiating effect with regard to the natural defensive reactions, which are only triggered from the time when attack by a pathogenic agent effectively takes place.

The advantage thereof is that the metabolism of the plant is not diverted toward the deployment of defensive reactions at a time when this deployment is pointless; this metabolism is alerted and it is only when the plant is the subject of an attack that it mobilises its defenses, this being done in a much more intense way than in the absence of treatment.

It follows that the process for stimulating the natural defenses of agronomically useful plants is characterized in that it comprises the application, in particular the foliar application, to the plants of the type in question, in particular those from the group defined above, of an effective amount of at least one oligo β 1–3 glucan, this effective amount being lower than those which directly induce defensive reactions.

The oligo β 1–3 glucans employed in the context of the aforesaid process are composed of 3 to 250, preferably of 3 to 50 and more preferably still of 3 to 30 monosaccharide units, their molecular mass consequently ranging from 540 to 45,000 Daltons.

The "effective amount" is defined by the amount of at least one oligo β 1–3 glucan which it is advisable to apply per hectare of crop to be treated in order to confer, on the plants of this crop, the acquired systemic resistance which has just been discussed.

It is, in the case of wheat, from 1 to 200 g, preferably from 4 to 80 g.

In other words, a subject matter of the invention is the use, in potentiating and stimulating the natural defenses of agronomically useful plants, of a plant protection composition comprising one or more oligo β 1–3 glucans composed of 3 to 250, preferably of 3 to 50 and more preferably of 3 to 30 monosaccharide units, the characteristics of concentration of oligo β 1–3 glucans and of use of this composition being chosen so that it contributes, per hectare of crop, an amount of oligo β 1–3 glucans lower than that which directly induces the natural defensive reactions, this amount being in practice from 1 to 200 g, preferably from 4 to 80 g per hectare in the case of cereals and in particular of wheat.

The composition is employed by application, in particular by foliar spraying, on one or two occasions at the early growth stages, in particular at the 2-leaf stage.

The precise moment of the application or applications will be chosen in particular as a function of the plant treated and of its growth stage.

The composition employed is generally aqueous in the case of foliar application; it comprises not only the active substance composed of the oligo β 1–3 glucan or glucans but also the conventional constituents of this type of composition, the concentration of active substance in the composition being from 0.001 to 0.02 g/l, preferably from 0.002 to 0.01 g/l in the case of cereals.

In drawing up the aforesaid composition, it is possible to use, instead of water, a vehicle chosen from the group consisting of mineral and vegetable oils, liquid fatty substances and alcohols, in particular propylene glycol and glycerol.

The conventional constituents of the aforesaid compositions are chosen, according to the plants to be treated, from the group consisting of solvents, surface-active agents, dispersing agents and solid fillers.

The volume of composition employed per hectare is from 10 to 1000 liters and generally of the order of 500 liters.

In an advantageous embodiment, the aforesaid plant protection composition comprises, in combination with the oligo β 1–3 glucans, at least one other plant protection product chosen from the group consisting of fungicides and insecticides.

Another subject matter of the invention is a concentrate in the form of a liquid or in the form of a powder or of granules, suitable for providing, by dilution with an appropriate amount of solvent, in particular of water, the composition used in accordance with the invention.

To prepare the aforesaid oligo β 1–3 glucans, it is possible to hydrolyse β 1–3 glucans, which are polysaccharides with a variable molecular weight of 60,000 to more than 1 million Daltons; these polysaccharides are composed essentially of D-glucose units connected specifically via β-glucoside bonds between the 1-carbon of the first glucose group and the 3-carbon of the second glucose group; these bonds are consequently β(1–3) bonds; they are linear polysaccharides which can carry β 1–6 branches and which have up to 10,000 monosaccharide units per molecule.

The β 1–3 glucans have various origins.

They can be extracted from bacteria, in particular from *Alcaligenes faecalis*, the extract in question being named curdlan, from fungi, in particular from *Schizophyllum commune* (the extract being schizophyllan), from *Sclerotium glucanium* (the extract being scleroglucan), other fungal extracts being pachyman, lichenan (extracted from *Cetraria islandica*), paramylon and lentinan (extracted from *Lentinus edodes*), from yeasts, in particular from *Saccharomyces cerevisae*, the extracts thus obtained being yeast glucan and zymosan, and from various plants, in particular from algae and from cereals, the corresponding extracts being denoted by "seaweed β-glucan" and "cereal β-glucan", other extracts being callose (extracted, for example, from graminaceous pollen grains).

The β 1–3 glucans can be hydrolysed enzymatically or with acid.

The β 1–3 glucans can be enzymatically degraded by use of β-glucanases extracted from yeasts of the *Saccharomyces cerevisiae* type or from mollusks.

Mention may be made, among these β-glucanases, of EC 3.2.1.21 or EC 3.2.1.6.

The desired oligosaccharide fraction is isolated by ultrafiltration from the hydrolysate thus obtained.

It is pointed out that the oligo β 1–3 glucans targeted in the context of the invention can also be prepared by chemical synthesis by employing the Koenig-Knorr reaction.

A first stage in this reaction consists of the acetylation of β D-glucose under warm conditions in sodium acetate ($CH_3COONa$).

In a second stage, the β D-glucopentacetate thus obtained is subjected to the Koenig-Knorr reaction.

The non-limiting examples which follow are given with respect in particular to advantageous embodiments.

EXAMPLE 1

Preparation of an Oligo β 1–3 Glucan Composed of a Hydrolysate Known as H13

The starting material is composed of curdlan which is a β(1–3) glucan extracted from a bacterium, namely *Alcaligenes faecalis*; curdlan is sold by the Company Sigma Chimie under the reference C 7821.

20 g of curdlan are dissolved in 2 liters of demineralized water.

This solution is thermostatically controlled at 40° C.; 80 units of the aforesaid enzyme are added thereto.

The combined mixture is maintained at 40° C. for 2 hours and 45 minutes.

The solution obtained is subsequently ultrafiltered in a tangential ultrafiltration device sold by the Company Millipore under the trade name Pellicon which is equipped with a cartridge with a porosity of 5000 Daltons.

The inlet pressure is 3 bar.

During this ultrafiltration, the volume to be ultrafiltered is kept constant at 2 liters by addition of a further 3 liters of demineralized water.

The ultrafiltrate with a volume of 4 liters obtained on conclusion of this ultrafiltration operation comprises the oligo β 1–3 glucans with a molecular mass of less than 5000 Daltons; as it is known that the molecular mass of the monosaccharide unit is approximately 180, the oligo β 1–3 glucans present in the ultrafiltrate are composed of at most 30 monosaccharide units. The solution is subsequently concentrated to a volume of 50 ml by evaporation at 80° C. using a device with the trade name Rotovapor and then lyophilized.

16 g of a cream-colored powder are obtained, which constitutes the hydrolysate H13.

Analysis by amperometry-coupled ion chromatography using the ion-exchange resin sold by the Company Dionex Chemical Corp. under the trade name Dionex shows that the constituent oligo β 1–3 glucans of the aforesaid powder in fact have 2 to 30 monosaccharide units, the mean degree of polymerization being from 3 to 15.

EXAMPLE 2

Preparation of an Oligo β 1–3 Glucan Composed of an Extract Known as H11

The starting material is a seaweed named *Laminaria digitata*.

1 l of 0.3% sulfuric acid is gradually added to 300 g of fresh seaweed of *Laminaria digitata* type collected in the month of August in the fresh or dry form.

The operation is carried out on a water bath at a temperature of approximately 70° C. for 2 hours and 30 minutes with stirring.

This operation is repeated twice.

The extract obtained is clarified by filtration through a filter with a porosity of 1.2 μm.

The liquid resulting from this filtration is subjected to tangential ultrafiltration through a membrane with a porosity of 50,000 Daltons.

The ultrafiltration is carried out while maintaining a pressure of 1 bar.

An ultrafiltrate with a pH of 5.5 is thus obtained exhibiting a volume of approximately 0.8 liter. This ultrafiltrate is subjected to dialysis over a cellulose ester membrane with a porosity equal to 500 Daltons.

A dialysate is obtained, which dialysate is concentrated to a volume of 100 ml by evaporation at 80° C. using a device of Rotovapor type and then lyophilized.

7 g of a cream-colored powder are obtained, which powder constitutes the extract H11.

Analysis by amperometry-coupled ion chromatography using an ion-exchange resin sold by the Company Dionex shows that the constituent oligo β 1–3 glucans of the aforesaid powder in fact have 3 to 30 monosaccharide units, the mean degree of polymerization being 20 to 30.

EXAMPLE 3
Preparation of an Oligo β 1–3 Glucan Composed of a Hydrolysate Known as H14

The starting material is zymosan.

An amount of 20 g of zymosan, which is a β 1–3 glucan extracted from *Saccharomyces cerevisiae* sold by the Company Sigma Chimie under the reference Z 4250, is dissolved in 2 liters of demineralized water.

20.4 g of a 96% concentrated sulfuric acid solution are added to this solution, so as to have a final $SO_4H_2$ concentration of 0.1M.

The mixture is maintained at 75–80° C. for 6 hours.

The medium is subsequently neutralized to pH 6 by addition of a 50% sodium hydroxide solution.

Tangential ultrafiltration is carried out using the device used in Example 1 equipped with a cartridge with a porosity of 5000 Daltons; the inlet pressure is 3 bar, this pressure being maintained during the ultrafiltration, which allows molecules with a molecular weight slightly greater than the theoretical cut-off threshold imposed by the cartridge with a porosity of 5000 Daltons to pass; the ultrafiltrate obtained is subjected to an additional ultrafiltration using the same ultrafiltration device but equipped with a cartridge with a porosity of 500 Daltons, by which the solution is desalinated.

The solution resulting from this operation is concentrated to a volume of 50 ml by evaporation at 80° C. using the device of Rotovapor type used in Example 1 and then lyophilized.

15 g of a cream-colored powder are thus obtained, which powder is composed of oligo β 1–3 glucans having a molecular mass of 500 to 5400 Daltons, that is to say of 3 to 30 monosaccharide units; this powder constitutes the hydrolysate H14.

The yield is 60 to 75% with respect to the starting material.

Analysis by amperometry-coupled ion chromatography using the ion-exchange resin sold by the Company Dionex Chemical Corp. under the trade name Dionex shows that the constituent oligo β 1–3 glucans of the aforesaid powder effectively have from 30 to 30 monosaccharide units, the mean degree of polymerization being from 4 to 10.

EXAMPLE 4
Preparation of an Oligo β 1–3 Glucan Composed of a Hydrolysate Known as H30

The starting material is composed of lichenan, which is a β 1–3 glucan extracted from a fungus, *Cetraria islandica*, sold by the Company Sigma Chimie under the reference L6133.

Use is made, as enzyme, of Cereflo, which is a β-glucanase preparation produced by fermenting a bacterial strain of *Bacillus subtilis* type and is sold by the Company Novo.

10 g of lichenan are dissolved in 2 liters of 25 demineralized water.

100 units of the aforesaid enzyme are added to this solution, which is thermostatically controlled at 30° C.

The combined mixture is maintained at 30° C. for 2 hours.

The solution is subsequently ultrafiltrated in a tangential ultrafiltration system sold by the Company Millipore under the trade name Pellicon which is equipped with a cartridge with a porosity of 10,000 Daltons.

During this ultrafiltration, the volume to be ultrafiltered is rinsed with a further 2 liters of demineralized water.

The ultrafiltrate with a volume of 4 liters obtained on conclusion of this ultrafiltration operation comprises the oligo β 1–3 glucans with a molecular mass of less than 10,000 Daltons; as it is known that the molecular mass of the monosaccharide unit is approximately 180, the oligo β 1–3 glucans present in the ultrafiltrate are composed of at most 50 monosaccharide units.

The solution is subsequently concentrated to a volume of 50 ml by evaporation at 80° C. using a device with the Rotovapor trade mark and then lyophilized.

8 g of a cream-colored powder are obtained, which powder constitutes the hydrolysate H30.

Analysis by amperometry-coupled ion chromatography using the ion-exchange resin sold by the Company Dionex Chemical Corp. under the trade name Dionex shows that the constituent oligo β 1–3 glucans of the aforesaid powder effectively have from 3 to 50 monosaccharide units, the mean degree of polymerization 20 being from 10 to 40.

EXAMPLE 5
Concentrated Aqueous Concentration Based on Extract H11

This concentrated composition essentially comprises the following constituents:

| | |
|---|---|
| Extract H11 | 200 g |
| Tween 80 surface-active agent | 5 g |
| Preserving agent (sodium methylparaben) | 5 g |
| Water | 790 g |
| | 1000 g |

For use, this concentrated composition comprising 20% by weight of active substance can be diluted with a sufficient amount of water to bring the concentration of active material in the final mixture to a value of 0.01 g/l.

The ready-for-use composition thus obtained can be employed by spraying onto the leaves of the plants to be treated.

EXAMPLE 6
Composition in the Form of a Powder Based on the Hydrolysate H13

It is a water-soluble composition which is provided in the form of a powder comprising the active material and the conventional constituents.

It is constituted as shown below:

| | |
|---|---|
| Hydrolysate H13 | 200 g |
| Kaolin as inorganic filler | 500 g |
| Preserving agent (sodium methylparaben) | 5 g |
| Purified starch as anti-caking agent | 295 g |
| | 1000 g |

For use by spraying, this powder comprising 20% by weight of active substance can be dissolved in a proportion of 10 g in 1000 ml of water.

EXAMPLE 7
Concentrated Aqueous Composition Based on Hydrolysate H14

This concentrated composition essentially comprises the following constituents:

| | |
|---|---|
| Hydrolysate H14 | 200 g |
| Tween 80 surface-active agent | 5 g |
| Preserving agent (sodium methylparaben) | 5 g |
| Water | 790 g |
| | 1000 g |

For use, this concentrated composition comprising 20% by weight of active substance can be diluted with a sufficient amount of water to bring the concentration of active material in the final mixture to a value of 0.01 g/l.

The ready-for-use composition thus obtained can be employed by spraying onto the leaves of the plants to be treated.

EXAMPLE 8
Composition in the Form of a Powder Based on the Hydrolysate H30

It is a water-soluble composition which is provided in the form of a powder comprising the active material and the conventional constituents.

It is constituted as shown below:

| | |
|---|---|
| Hydrolysate H30 | 200 g |
| Kaolin as inorganic filler | 500 g |
| Preserving agent (sodium methylparaben) | 5 g |
| Purified starch as anti-caking agent | 295 g |
| | 1000 g |

For use by spraying, this powder comprising 20% by weight of active substance can be dissolved in a proportion of 10 g of H30 in 1000 ml of water.

\*

\* \*

The effectiveness of the oligo β 1–3 glucans constituting the hydrolysate H13 and the extract H11 was demonstrated on young wheat plants infected with septoria disease; furthermore, the potentiation of the natural defenses which are obtained using the extract H11 and the hydrolysate H13 in the case of cultures of tobacco cells was shown.

The corresponding experiments are described in Examples 9 to 12.

EXAMPLE 9
Study of the Effectiveness of the Hydrolysate H13 in the Case of Wheat Infected with *Septoria tritici*

For this study, use is made of 200 soft winter wheat plantlets of "Tendral" type known for its susceptibility with regard to *Septoria tritici*.

These plantlets are grown in 20 trays each comprising a batch of 10 plantlets.

5 sets are formed which are respectively denoted A, B, C, D and E and are each composed of 4 trays, in other words 4 batches of 10 plantlets.

In each set the first and second batches of plantlets, which are control batches, are treated by foliar spraying at the 2-leaf growth stage (GS 12 according to the Zadocks scale) by distilled water in the presence of 0.1% of Tween 20, the third and fourth batches are treated by foliar spraying at the 2-leaf growth stage (GS 12 according to the Zadocks scale) with 5 ml of a first composition in accordance with the invention comprising the hydrolysate H13 as active substance.

The aforesaid composition comprises in distilled water in the presence of Tween 20:

in the experiment on the A set, 1 mg/l of hydrolysate H13, in the experiment on the B set, 2 mg/l of hydrolysate H13, in the experiment on the C set, 10 mg/l of hydrolysate H13, in the experiment on the D set, 100 mg/l of hydrolysate H13, in the experiment on the E set, 1000 mg/l of hydrolysate H13.

After the aforesaid spraying treatments, the plantlets of the four batches of each set are kept at room temperature for 4 hours in order to allow the droplets of products at the surface of the leaves to dry. They are subsequently placed in a controlled-environment chamber at 19° C. during the day and 17° C. during the night, with a photoperiod of 12 hours of light followed by 12 hours of darkness, at a relative humidity of 65%.

48 hours after this treatment, inoculation is carried out by spraying, at the first and third batches of each set, a suspension in water in the presence of 0.1% of Tween 20 comprising $10^5$ pycnospores per ml of a *Septoria tritici* strain.

The second and fourth batches of each set are subjected to the same inoculation with pathogenic agent 72 hours after the treatment with the hydrolysate H13.

The plantlets of the control batches and those of the batches which have been inoculated with *Septoria tritici* are placed in a controlled-environment chamber at 19° C. during the day and 17° C. during the night, with a photoperiod of 12 hours of light followed by 12 hours of darkness, and a relative humidity of 100% during the first 96 hours and of 85% subsequently.

21 days after respectively the first and second series of inoculation with *Septoria tritici*, the wheat plantlets of the five sets of four batches are inspected.

The effectiveness of the products is characterized, on the one hand, by the percentage of protection PP and, on the other hand, by the intensity of infection II, both expressed as percent.

The two quantities are defined with respect to the control batches.

The "percentage of protection" is calculated from the following formula:

$$\frac{\begin{array}{c}\text{Number of control plants}\\\text{exhibiting at least one}\\\text{foliar necrosis}\end{array} - \begin{array}{c}\text{Number of treated plants}\\\text{exhibiting at least one}\\\text{foliar necrosis}\end{array}}{\begin{array}{c}\text{Number of control plants exhibiting}\\\text{at least one foliar necrosis}\end{array}} \times 100$$

The "intensity of infection" is calculated from the following formula:

$$\frac{\begin{array}{c}\text{Proportion of the leaf}\\\text{area which is necrotic}\\\text{on control plants}\end{array} - \begin{array}{c}\text{Proportion of the leaf}\\\text{area which is necrotic}\\\text{on treated plants}\end{array}}{\begin{array}{c}\text{Proportion of the leaf area which}\\\text{is necrotic on control plants}\end{array}} \times 100$$

The results of all these determinations are combined in Table I.

TABLE I

| Hydro-lysate employed | Set (concentration of hydrolysate in the treatment composition) | Results recorded 21 days after | | | |
|---|---|---|---|---|---|
| | | Inoculation of the spores 48 hours after treatment | | Inoculation of the spores 72 hours after treatment | |
| | | PP % | II % | PP % | II % |
| H13 | A  1 mg/l | 6.4 | 4.6 | 12.3 | 16.8 |
| | B  2 mg/l | 34.5 | 30.4 | 58.4 | 85.4 |
| | C  10 mg/l | 27.5 | 20.0 | 39.7 | 65.6 |
| | D  100 mg/l | 3.3 | 4.5 | 21.9 | 28.8 |
| | E  1000 mg/l | 0 | 0 | 0 | 0 |

It results from the examination of the results combined in Table I that the spraying of H13 results in a decrease in infection by *Septoria tritici*, that the treatment must be carried out before possible infection by a pathogenic agent; thus, the results recorded for an inoculation at 72 hours after the treatment are better than those recorded for an inoculation at 48 hours after the treatment, that the concentrations of the compositions applied are advantageously from approximately 2 to approximately 10 mg/l, values for which, from Example 12 below, there is no or virtually no elicitation of the defensive reactions.

EXAMPLE 10
Study of the Effectiveness of the Extract H11 in the Case of Wheat Infected with *Septoria tritici*

For this study, use is made of 200 soft winter wheat plantlets of "Tendral" type known for its susceptibility with regard to *Septoria tritici*.

These plantlets are grown in 20 trays each comprising a batch of 10 plantlets.

5 sets are formed which are respectively denoted A, B, C, D and E and are each composed of 4 trays, in other words 4 batches of 10 plantlets.

In each set
the first and second batches of plantlets, which are control batches, are treated by foliar spraying at the 2-leaf growth stage (GS 12 according to the Zadocks scale) by distilled water in the presence of 0.1% of Tween 20, the third and fourth batches are treated by foliar spraying at the 2-leaf growth stage (GS 12 according to the Zadocks scale) with 5 ml of a first composition in accordance with the invention comprising the extract H11 as active substance.

The aforesaid composition comprises in distilled water in the presence of Tween 20:
in the experiment on the A set, 1 mg/l of extract H11,
in the experiment on the B set, 2 mg/l of extract H11,
in the experiment on the C set, 10 mg/l of extract H11,
in the experiment on the D set, 100 mg/l of extract H11,
in the experiment on the E set, 1000 mg/l of extract H11.

After the aforesaid spraying treatments, the plantlets of the four batches of each set are kept at room temperature for 4 hours in order to allow the droplets of products at the surface of the leaves to dry. They are subsequently placed in a controlled-environment chamber at 19° C. during the day and 17° C. during the night, with a photoperiod of 12 hours of light followed by 12 hours of darkness, at a relative humidity of 65%.

48 hours after this treatment, inoculation is carried out by spraying, at the first and third batches of each set, a suspension in water in the presence of 0.1% of Tween 20 comprising $10^5$ pycnospores per ml of a *Septoria tritici* strain.

The second and fourth batches of each set are subjected to the same inoculation with pathogenic agent 72 hours after the treatment with the extract H11.

The plantlets of the control batches and those of the batches which have been inoculated with *Septoria tritici* are placed in a controlled-environment chamber at 19° C. during the day and 17° C. during the night, with a photoperiod of 12 hours of light followed by 12 hours of darkness, and a relative humidity of 100% during the first 96 hours and of 85% subsequently.

21 days after respectively the first and second series of inoculation with *Septoria tritici*, the wheat plantlets of the five sets of four batches are inspected.

The effectiveness of the products is characterized, on the one hand, by the percentage of protection PP and, on the other hand, by the intensity of infection II, both expressed as percent.

The two quantities are defined with respect to the control batches.

The "percentage of protection" is calculated from the following formula:

$$\frac{\begin{array}{c}\text{Number of control plants}\\\text{exhibiting at least one}\\\text{foliar necrosis}\end{array} - \begin{array}{c}\text{Number of treated plants}\\\text{exhibiting at least one}\\\text{foliar necrosis}\end{array}}{\begin{array}{c}\text{Number of control plants exhibiting}\\\text{at least one foliar necrosis}\end{array}} \times 100$$

The "intensity of infection" is calculated from the following formula:

$$\frac{\begin{array}{c}\text{Proportion of the leaf}\\\text{area which is necrotic}\\\text{on control plants}\end{array} - \begin{array}{c}\text{Proportion of the leaf}\\\text{area which is necrotic}\\\text{on treated plants}\end{array}}{\begin{array}{c}\text{Proportion of the leaf area which}\\\text{is necrotic on control plants}\end{array}} \times 100$$

The results of all these determinations are combined in Table II.

TABLE II

| Extract employed | Set (concentration of hydrolysate in the treatment composition) | Results recorded 21 days after | | | |
|---|---|---|---|---|---|
| | | Inoculation of the spores 48 hours after treatment | | Inoculation of the spores 72 hours after treatment | |
| | | PP % | II % | PP % | II % |
| H11 | A  1 mg/l | 32.2 | 50.7 | 30.1 | 45.5 |
| | B  2 mg/l | 38.5 | 67.3 | 39.7 | 73.7 |
| | C  10 mg/l | 24.1 | 33.1 | 29.5 | 62.7 |
| | D  100 mg/l | 12.0 | 18.3 | 24.9 | 30.0 |
| | E  1000 mg/l | 0 | 0 | 0 | 0 |

It results from the examination of the results combined in Table II that the spraying of H11 results in a decrease in infection by *Septoria tritici*, that the treatment must be carried out before possible infection by a pathogenic agent; thus, the results recorded for an inoculation at 72 hours after the treatment are better than those recorded for an inoculation at 48 hours after the treatment, that the concentrations of the compositions applied are advantageously from approximately 2 to approximately 10 mg/l, values for which, from Example 12 below, there is no or virtually no elicitation of the defensive reactions.

EXAMPLE 11
Study of the Agronomic Effectiveness of the Extract H11 in the Case of Wheat Septoria Disease The fungus responsible for the disease is *Septoria tritici*.

The material is employed in the form of the composition identified in Example 5.

The experimentation is carried out under field conditions on a variety susceptible to septoria disease and makes it possible to compare several doses of active material, namely 0.4 g/ha, 4 g/ha, 20 g/ha, 40 g/ha, 60 g/ha and 80 g/ha.

Each dose is tested on four plots of 20 m². Four additional plots act as control.

The effectiveness is assessed by the intensity of infection, which is calculated by the following formula:

$$\frac{\text{Proportion of the leaf area which is necrotic on control plants} - \text{Proportion of the leaf area which is necrotic on treated plants}}{\text{Proportion of the leaf area which is necrotic on control plants}} \times 100$$

The composition is applied by foliar spraying, which is carried out at the BBCH 30 stage with a volume of 250 l/ha.

Infection takes place naturally.

The proportion of the area attacked in the control plots, that is to say untreated plots, is 17%.

These experiments were repeated three times and the mean of the results is collated in Table III.

TABLE III

| Dose/ha | Effectiveness in % |
| --- | --- |
| 0.4 g | 6 |
| 4 g | 20 |
| 20 g | 40 |
| 40 g | 41 |
| 60 g | 40 |
| 80 g | 35 |

Examination of the values combined in Table III shows that the best results are obtained by doses of 20 to 60 g/ha.

EXAMPLE 12
Experiments Showing the Potentiation of the Natural Defenses of the Plants by the Extract H11 and the Hydrolysate H13

Two experiments were carried out.

In a first experiment, for the purpose of studying the direct eliciting effect of the products H11 and H13, compositions with increasing concentrations of H11 and of H13, namely:

for H11, compositions with concentrations successively equal to 2 mg/l, 10 mg/l, 20 mg/l, 50 mg/l and 200 mg/l, for H13, compositions with concentrations successively equal to 2 mg/l, 10 mg/l, 50 mg/l and to 200 mg/l, were applied to cultures of BY tobacco cells.

For each composition, four markers of the defensive reactions were tested, namely:

the phenylammonia lyase (PAL) activity, which enzyme is a key enzyme in the synthesis of phytoalexins in plants, the O-methyl transferase (OMT) activity, which enzyme is an enzyme involved in the synthesis of lignin, the lipoxygenase (LOX) activity, which enzyme is an enzyme involved in the generation of methyl jasmonate, that is to say of a component in the signaling cascade which ends in the activity of the defensive genes, and the salicylic acid (SA) content, which acid is another secondary messenger involved in the defensive reactions.

The results are expressed in the form of an induction factor for the markers studied representing the ratio of the values measured in the elicited cells to those measured in nonelicited control cells.

The results of these measurements, which are carried out from 4 to 48 hours after the beginning of the incubation, are combined in Table IV below.

TABLE IV

| Oligo β 1–3 glucans employed | | Induction factor for the defense marker | | | |
| --- | --- | --- | --- | --- | --- |
| | | PAL | OMT | LOX | SA |
| H11 | 2 mg/l | NS* | NS | NS | NS |
| | 10 mg/l | NS | NS | NS | NS |
| | 20 mg/l | 33 | | NS | |
| | 50 mg/l | 90 | | 2.5 | |
| | 200 mg/l | 150 | 3.0 | 8.0 | 35.0 |
| H13 | 2 mg/l | NS | | | NS |
| | 10 mg/l | 67 | | | NS |
| | 50 mg/l | 176 | | | 30.0 |
| | 200 mg/l | 170 | | | 30.0 |

*NS = not significant

Examination of these results shows that the products H11 and H13 elicit defensive reactions in the treated cells, these elicitations being reflected by the accumulation of the markers when said products are used at concentrations ranging from 20 to 200 mg per liter; on the other hand, on the basis of the PAL and SA markers, these reactions are not induced to a significant extent when the concentration of elicitor, that is to say of product H11 or H13, is 2 or 10 mg per liter.

In a second experiment, cultures of the same BY tobacco cells are pretreated on the day following subculturing by using compositions exhibiting concentrations of extract H11 equal to 2 or to 10 mg per liter.

Six days later, these cultures and non-pretreated control cultures are treated with a composition comprising oligopectins at a concentration of 40 mg per liter.

This is a situation which mimics attack by a pathogenic agent.

The kinetics of accumulation of salicylic acid (SA) are then monitored from 4 to 48 hours after the treatment.

These measurements show that the cells of the control cultures accumulate SA up to contents which do not exceed 300 ng per gram of fresh mass (FM).

They also show that the pretreatment with H11 very strongly stimulates, in an entirely unexpected way, the accumulation of salicylic acid when the plant is elicited six days later with oligopectins; this is because an accumulation of SA of 2900 ng per gram of FM is recorded in the tobacco cells thus treated when the concentration of H11 during the pretreatment is 2 mg per liter and an accumulation of SA of 700 ng per gram of FM is recorded in the tobacco cells thus treated when the concentration during the pretreatment is 10 mg per liter.

The potentiating effect on a defensive reaction obtained by virtue of the use in accordance with the invention is thus demonstrated.

It should be understood that the foregoing relates only to preferred embodiments of the present invention and that numerous modifications or alterations may be made therein without departing from the spirit and the scope of the present invention as defined in the following claims.

What is claimed is:

1. A composition useful in potentiating and stimulating natural defensive reactions of plants to a pathogenic agent, comprising a vehicle and one or more oligo β(1–3) glucans with an average degree of polymerisation from 3 to 15 and composed of from 2 to 30 monosaccharide units at a concentration from 1 mg/l to 20 mg/l.

2. The composition of claim 1, wherein the vehicle is water, oil, a liquid fatty substance or alcohol.

3. The composition of claim 1, wherein the vehicle is water.

4. The composition of claim 1, further comprising solvents, surface-active agents, dispersing agents or solid fillers.

5. The composition of claim 1, further comprising at least one other plant protection product.

6. A concentrate in the form of a liquid, powder or granule, wherein the concentrate may be diluted with a solvent to provide the composition of claim 1.

7. The concentrate of claim 6, wherein the solvent is water.

8. A composition according to claim 1 wherein the concentration of the one or more oligo β(1–3) glucans with an average degree of polymerisation from 3 to 15 and composed of from 2 to 30 monosaccharide units, is from 2 mg/l to 10 mg/l.

9. A method to potentiate and stimulate in an agronomically useful plant natural defense reactions which are normally developed by the plant when the plant has first contact with a pathogenic agent, the method comprising applying to the plant before the first contact with the pathogenic agent, a composition comprising one or more oligo β(1–3) glucans with an average degree of polymerisation from 3 to 15 and composed of from 2 to 30 monosaccharide units and a vehicle, the one or more oligo β(1–3) glucans being present in the composition at a concentration from 1 mg/l to 20 mg/l.

10. The method of claim 9, wherein the plants are selected from the group consisting of cereals, vegetables, oleaginous plants, tobacco, vines and fruits.

11. The method of claim 9, wherein the plants are cereals.

12. The method of claim 9, wherein the plant is a cereal and the cereal is wheat.

13. The method of claim 9, wherein the vehicle is water, oil, a liquid fatty substance or alcohol.

14. The method of claim 9, wherein the composition further comprises solvents, surface-active agents, dispersing agents or solid fillers.

15. The method of claim 9, wherein the composition further comprises at least one other plant protection product.

16. The method of claim 9, wherein the composition is applied to leaves of the plant.

17. The method of claim 9, wherein the one or more oligo β 1–3 glucans in the composition are present in a concentration of about 2 mg/l to 10 mg/l.

* * * * *